United States Patent
Fuchs

(10) Patent No.: US 6,886,556 B2
(45) Date of Patent: May 3, 2005

(54) DISPENSER FOR MEDIA

(75) Inventor: Karl-Heinz Fuchs, Rodolfzell (DE)

(73) Assignee: Ing. Erich Pfeiffer GmbH, Radolfzell (DE)

(*) Notice: Subject to any disclaimer, the term of this patent is extended or adjusted under 35 U.S.C. 154(b) by 185 days.

(21) Appl. No.: 10/246,657

(22) Filed: Sep. 18, 2002

(65) Prior Publication Data

US 2003/0052196 A1 Mar. 20, 2003

(30) Foreign Application Priority Data

Sep. 18, 2001 (DE) .......................... 101 46 815

(51) Int. Cl.[7] .............................................. B67D 5/06
(52) U.S. Cl. ............................ 128/200.14; 128/205.23; 222/71
(58) Field of Search .................... 128/200.14, 205.23; 222/71

(56) References Cited

U.S. PATENT DOCUMENTS

| | | | |
|---|---|---|---|
| 4,736,871 A | * 4/1988 | Luciani | ........................ 222/25 |
| 6,138,669 A | 10/2000 | Rocci, Jr. et al. | ........ 128/200.23 |
| 6,161,731 A | 12/2000 | Sigg | ........................... 222/158 |
| 6,196,218 B1 | 3/2001 | Voges | ..................... 128/200.14 |
| 6,196,219 B1 | 3/2001 | Hess et al. | ............. 128/200.21 |
| 6,454,185 B2 | * 9/2002 | Fuchs | ......................... 239/338 |
| 6,578,741 B2 | * 6/2003 | Ritsche et al. | ......... 222/153.12 |
| 2002/0043568 A1 | 4/2002 | Hess et al. | ..................... 239/69 |

FOREIGN PATENT DOCUMENTS

| | | |
|---|---|---|
| DE | 19835941 | 2/2000 |
| EP | 0 821 975 A1 | 2/1998 |
| EP | 0 923 957 B1 | 10/2001 |
| EP | 1 184 083 B1 | 7/2003 |
| WO | WO 00/01612 | 1/2000 |
| WO | WO 00/69496 | 11/2000 |
| WO | WO 01/45768 A2 | 6/2001 |

* cited by examiner

Primary Examiner—Harry B. Tanner
(74) Attorney, Agent, or Firm—D. Peter Hochberg; Katherine R. Vieyra; Sean Mellino

(57) ABSTRACT

The problem of the invention is to so develop known dispensers, that it is possible to very precisely determine the actual discharged medium volume.

A dispenser according to the invention has a media path, which leads from a medium storage container to a discharge opening. A delivery device for delivering medium is located in said media path. The media reservoir stores a medium, particularly a fluid, which preferably incorporates at least one pharmaceutical substance. A media discharge can be brought about by means of an operating means. According to the invention, on the dispenser is provided an electronic detecting device for detecting a quantity representing the amount of medium discharged.

23 Claims, 3 Drawing Sheets

DISPENSER FOR MEDIA

BACKGROUND OF THE INVENTION

The present invention relates to a dispenser for media, particularly for discharge of fluids. Such dispensers are used for discharging fluids containing at least one pharmaceutical substance in a clearly defined dose, particularly by atomized spraying.

The atomized discharge of such fluids can take place in intranasal manner. Preferably a precisely dosed, equal medium quantity is discharged into each of the two nostrils. Pharmaceutical substances or substance combinations, which can be discharged in this way, can e.g. be opiates, but in general terms reference is also made to other active substances, particularly anticephalalgics and analgesics. They can be used in medicaments for the treatment of chronic illnesses and/or requiring a continuous application (e.g. diabetes, cardiovascular diseases, etc.). The suitability of an active substance for such a discharge is dependent on the fact that the active substance can be absorbed by the mucosa, particularly the nasal mucosa. The introduction of the medium though the nasal mucosa is particularly advantageous, because it ensures a rapid absorption and rapid introduction into the body and particularly the cerebral region of the body.

Such dispensers have a storage container storing the corresponding medium. The storage container is linked by a media path with a dispenser discharge opening e.g. a spray nozzle. There is also an operable delivery device in the media path which delivers the medium from the storage container to the discharge opening. A delivery process takes place when an operating or actuating means is operated. The delivery device is generally constituted by a piston pump, so that the discharge medium quantity substantially corresponds to the volume of the working chamber of the piston pump. The piston pump are more particularly plunger pumps.

This quantity is not always reliable in establishing the quantity of the medium actually discharged. Firstly residual air quantities can be present in the pump piston, which is particularly the case after prolonged storage periods and prior to the first use of the dispenser, when priming of the dispenser is necessary. Priming is done by performing several discharge strokes until the flow path is completely filled with medium. It can also arise that on operating the dispenser no complete operating stroke is performed. It is known that often pumps are designed to force the user during each dispenser operation to perform a complete operating stroke and therefore also a complete discharge stroke of the delivery device. This is however, not always reliable.

OBJECT OF THE INVENTION

Therefore the object of the invention is to further develop dispensers in such a way that the actual discharge medium volume can be very precisely determined and other criteria of the discharge can be detected and processed.

SUMMARY OF THE INVENTION

A dispenser according to the invention has a media path leading from a medium storage container to a discharge opening. A delivery device for delivering medium is located in said media path. The media reservoir stores a medium, particularly a fluid, which preferably contains at least one pharmaceutical substance. The medium is discharged by operating an actuating means. The dispenser is provided with an electronic detection device for detecting a quantity representing the discharged medium quantity. By means of said detecting device, it is possible to detect the medium quantity actually discharged for each individual dispenser operation.

The detecting device comprises a flow volume meter located in the media path. The flow volume meter is preferably located between the delivery device and the discharge opening. It is particularly advantageous if the flow volume meter is located in an area of the medium path, where upstream there is only the discharge opening as a flow obstacle. This ensures that the specific medium volume flow actually passing through the discharge opening is detected.

The flow volume meter shall perform a quantitative flow measurement. It may be a thermal or inductive flow volume meter or a flow volume meter operating according to a pressure difference measuring method. The measuring range of the measuring method must be adapted to the volume of the medium to be discharged during one dispenser pump stroke. This volume is below 200 æl and is in particular between 30 and 150 æl. It shall be able to detect discharge which takes place within a short time interval, e.g. between 50 and 100 milliseconds. In addition, a high precision of measurement shall be ensured, because the discharged media are often those which contain pharmaceutical substances, which must be very precisely dosed, because e.g. in the case of an overdosage can give rise to health-prejudicing effects.

The delivery device can be designed as a manually operable reciprocating pump. By means of at least one sensor a signal at least indirectly representing the stroke path of the reciprocating piston can be detected. Furtheron, it is possible that the reaching of the upper dead centre position of a pump piston is detected by a limit switch, e.g. a keying switch, which is preferably constructed as a normally closed contact. Alternatively or additionally a further limit switch can be provided, which detects the leaving of the lower dead centre position of the pump.

By means of the limit sensor, detecting the upper dead centre position, it is possible to establish whether there has been a complete operation of the operating means and therefore a complete operating stroke of the pump. This measure can be used for balancing or adjusting and calibrating a flow volume meter. If a complete piston stroke is performed, the flow quantity detected by the flow volume meter must correspond to the volume of a piston stroke. For example, if additionally the leaving of the lower dead centre position is detected, it is then possible to establish whether the discharge has been performed in a single, complete, operating stroke. In particular such cases can be used for balancing or adjustment purposes for the detected flow volume meter signal. In particular, time drifts and similar characteristics, as well as the stochastic dispersion of the measuring signal of the measuring sensor can be partly compensated. It would also be possible by means of a path or displacement sensor to detect the path covered by the pump piston. On the basis of the displaced volume corresponding to this stroke path, it is then possible to determine the discharged medium quantity. This more particularly applies to fluid media, which are incompressible or can be looked upon as incompressible. The discharge quantity measurement effected indirectly through the path measurement can be additionally or alternatively carried out with respect to the flow volume measurement by means of a flow volume meter. On using both measuring methods, there can once again be a balancing of the two measurement results and it can be possible to increase the quality of the measurement result and precision.

Besides the detection of the discharged medium quantity, it is also possible to detect the time of dispenser operation in said detecting device. It is in particular possible to detect the time since the last dispenser operation. It is also possible to detect the time of the last operation or the date and time of the last operation. This detection can on the one hand be provided for recording the operations which have taken place, but on the other hand it is also possible for the dischargeable medium volume to take place as a function of preceding operations. It can e.g. be provided that in one operation only that medium quantity can be discharged which ensures that the discharged quantity over and beyond a certain time period does not exceed a specific, predetermined value. This can e.g. be appropriate if the medium contains addictive pharmaceutical substances or those having a lethal action in overdose and where a certain dosage over and beyond a certain period must not be exceeded. If at least there is a recording of the discharge behaviour of the dispenser, such information is preferably stored in the dispenser, particularly in the vicinity of the detecting device in such a way that it is filed that it can be polled and/or read out. If the discharge volume of a subsequent dispenser operation takes place on the basis of preceding dispenser operations and optionally on the basis of the time period which has elapsed since then, in the vicinity of the dispenser is provided a regulating device, which limits the maximum stroke of a pump.

In the vicinity of the discharge opening, it is possible to provide a measuring sensor, e.g. a temperature sensor. The sensor is in particular located in the immediate vicinity of the tip of a nose adaptor (olive) of the dispenser, in which the discharge opening is formed. It is possible to detect by means of the sensor whether a dispenser operation has taken place or should take place and whether the dispenser is placed at an intended application point, e.g. in the vicinity of a nasal ala. This measure can e.g. be used to prevent unintentional or unintended operations and uses of the dispenser as not to include the same in quantity detections. It is in particular possible to construct the sensor in such a way that it detects an ambient value or characteristic, such as the temperature, atmospheric humidity, brightness, etc. and no large time delay occurs during the measurements. Thus, a temperature sensor should e.g. not be located in the vicinity of a large thermal capacitance in order to be able to rapidly detect a change in the ambient temperature. As a function of the measuring signals of the sensor, it is consequently possible to conclude whether the application of the medium takes place at the intended application point, e.g. the nose. It is also possible to activate an operating barrier if it is established that there is no application at the intended application point or if an application is only permitted if it can be concluded that an application at the intended application point has been performed. Alternatively or additionally it is possible to only take account of such discharges in the detecting device, for which it is possible to conclude that they have been performed at the intended application point. The measuring sensor can in particular be a temperature sensor. However, a corresponding signal can also be detected by optical sensor technology or by measuring the composition of the ambient air (atmospheric humidity, $CO_2$ content).

By means of the sensor it is not only possible to detect at what point an application of the medium has taken place, it also being possible to establish the time pattern of the temperature of the medium or the medium storage area. Particularly in the case of thermally sensitive medicaments, it can be ensured that further media are not discharged, which e.g. as a result of thermal influences would have been modified in the meantime and are no longer suitable for use.

Additionally or alternatively to a regulating device for the discharge volume, it is also possible for the dispenser to have a switchable operating barrier. This operating barrier can in particular prevent a further operation of the dispenser within a time interval. The time interval can be determined as a function of quantities or values detectable in the detecting device, e.g. the detected discharged quantity.

It is also possible to provide in addition to the detecting device a data exchange device. The detecting device and data exchange device can be integrated into a single component, particularly a single electronic chip. The data exchange device is e.g. suitable to transmit signals or data detected in the detecting device to external data processing devices, especially in contactless manner. There can be a bidirectional data transmission. It is e.g. possible to use data transmission by means of infrared light or via transponders and the like. Data transmission by radio installations is also possible. Data transmission also permits a remote diagnosis, remote monitoring and/or remote treatment within local or non-local radio networks. If there is a bidirectional data transmission, the dispenser can also be interrogated from the outside and detected data can be interrogated. It is also possible to adjust or modify from the outside the operating state or parameters (duration of operating barriers, lifting or activating an operating barrier, discharge stroke volume, etc.), e.g. according to a doctor's prescription. The external data processing devices may include a base station and a evaluation station. The base station can be near the user of the dispenser and may include, besides storing, energy supply, memory and display functions, a remote data transmission module, e.g. a GSM modem, enabling a remote data transmission to a doctor's personal computer or an institution, for evaluation of the results of treatment and for amending it, if necessary.

On the operating means can be provided a sensor device permitting an identification and authentication of the user. The authentication of a user by means of invariable, endogenic features, e.g. fingerprints and ocular fundus, but also the inputting of a PIN code at a suitable input interface is suitable to check the justification to use the dispenser for each individual operation. This makes it possible to monitor the user particularly in those cases where the pharmaceutical substance is subject to a very precise observation and strict prescription rules, such as e.g. with opiates and other addictive medicaments.

These and further features can be gathered from the claims, description and drawings and the individual features, both singly and in the form of subcombinations, can be implemented in an embodiment of the invention and in other fields and can represent advantageous, independently protectable constructions for which protection is claimed here.

BRIEF DESCRIPTION OF THE DRAWINGS

The invention is described in greater detail hereinafter relative to a preferred embodiment shown in the drawings.

DETAILED DESCRIPTION OF THE PREFERRED EMBODIMENTS

Figure 1:
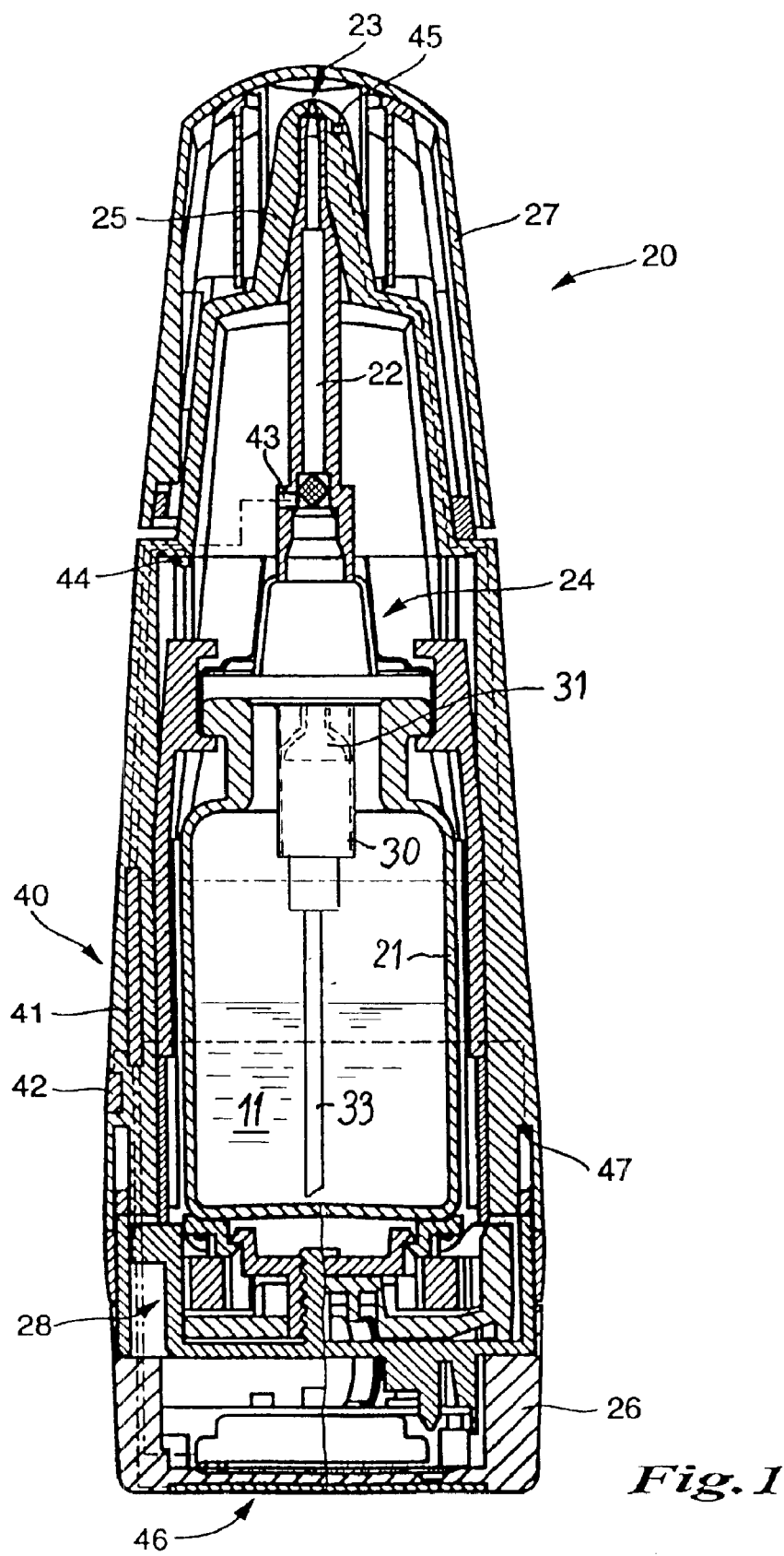
FIG. 1 shows in a diagrammatic part sectional representation of a dispenser.

FIG. 1 shows a dispenser suitable for the discharge of media to be administered to the nose of a person undergoing treatment. A medium 11 containing at least one pharmaceutical substance or substance combination is stored in a storage container 21 of the dispenser 20. The storage container 21 is retained in the interior of the dispenser 20. A media path 22 leads from the storage container 21 via a delivery device 24, which produces the discharge from the storage container, to the discharge opening 23 of the dispenser. The dispenser discharge opening 23 is situated at the tip of a nose olive or adapter 25, which is used for the application of the dispenser in the vicinity of the nostrils of the person to be treated. The discharge opening 23 is a spray nozzle to permit an atomized discharge of the medium 11. The media path 22 incorporates the medium delivery device 24, which delivers the medium from the storage container 21 to the discharge opening 23. The delivery device 24 is a manually operable single stroke plunger or reciprocating pump. It allows to accurately dose a discharged medium quantity. The dispenser 20 is operated by means of an operating means 26, which produces a discharge stroke during each operation. The operating means 26 is constructed as an operating trigger.

A detecting device 40 is provided comprising an evaluation unit 41 and a data transmission device 42. The data transmission device 42 is able to transmit data from the evaluation unit 41 to an external data processing station and vice versa. The data can be both recorded data and e.g. also programmable details, which are transmitted by the external data processing station to the evaluation unit 41, in order to influence the discharge from the dispenser as a function of predetermined, individually adjustable dosage details.

For detecting the discharged quantity of medium, the detecting device 40 has a flow volume meter 43 and a path sensor 47. The path sensor 47 detects the operating path of the operating means 26 and therefore the stroke of the pump 24 coupled thereto. This strokes serves as a measure for the discharged medium quantity. The flow volume meter 43, which can e.g. be constructed as a differential pressure meter or as an inductive or thermal flow volume meter, provides a direct measure for the medium quantity discharged as opposed to the indirect measure for the discharge quantity measured by the path sensor 47. Thus, the flow volume meter 43 is particularly located in an area of the media path 22, which is as close as possible to the discharge opening 23 and where there are minimum possibilities for leaks and other disturbances.

A temperature sensor 45 is provided as a measuring sensor in the immediate vicinity of the discharge opening 23 close to the tip of the nose olive 25. The temperature sensor 45 is positioned in such a way that between it and the external environment of the dispenser 20 a minimum thermal capacitance is formed, so that it can very rapidly detect temperature changes in the environment. This makes it possible to establish whether the nose olive is located in the vicinity of the patient's nose, because here due to the air flow of the air breathed out, the temperature must rise relatively accurately to a value in the range approximately of that of the human body temperature (37 to 42° C.). It is also possible to detect by means of the temperature sensor 45 whether the transportation and storage temperature have remained within ranges adapted to the medium. For this purpose the temperature data can be recorded considering temperature sensitivity and time of temperature exposure. Said recorded data can be read out prior to the delivery of the dispenser with the medium contained therein to the customer by means of the data transmission device 42 and can be checked. Thus, it is possible to control especially with medicaments where the life is very limited and very temperature-dependent, whether the quality of the medium is still completely adequate. The data transmission from the data transmission device to the fixed station can e.g. take place by means of corresponding infrared interfaces or transponders, but also by galvanic contact, e.g. a cable link.

The signal of a limit switch 44 can also be supplied to the evaluation unit 41 and it is then established whether there has been a complete discharge stroke of the delivery device 24. This possibility can be used to make a comparison with the evaluated signals of the flow volume meter 43 or path sensor 47 in the evaluation unit 41 of the detecting device 40. By means of a balancing of said sensor signals, it is e.g. possible to calibrate the same. It is possible via the dosing precision of the pump to conclude whether the volume of the medium quantity measured by the flow volume meter corresponds to the piston stroke volume, which is displaced in the corresponding cylinder during a complete discharge stroke. For this purpose the measurement difference should be very closed limited, because otherwise a defect is assumed requiring special checking. A corresponding e.g. optical and/or acoustic alarm message can then be generated. It is also possible for the evaluation unit 41 to detect who is using the dispenser 20. This can e.g. take place by means of a fingerprint sensor 46 detecting the fingerprint of the user on the operating means 26. It is also conceivable to use other sensors, e.g. a sensor located close to the discharge opening and e.g. suitable to detect the ocular fundus. The last-mentioned sensor can be particularly used if application is to take place in the vicinity of the eye of a patient. It is possible to only allow specific persons to use the dispenser.

To the extent that in the discharged medium quantity evaluation unit also detects the operating time, it is possible in quantity and time-dependent manner to limit or block operation of the dispenser. For this purpose the dosing device 28 is used in the embodiment shown. The dosing device 28 makes it possible to limit the maximum possible stroke path of the delivery device 24, which is fixed by the operating path of the operating means. The limitation can be such that in one extreme limitation state the action of an operating barrier is reached, so that no media discharge is possible, whilst in the other extreme a complete piston stroke can be performed so as to permit the discharge of one or more piston strokes. Thus, on the one hand an operating barrier is obtained for preventing an overdosage of the medicine. The operating barrier may be constructed as described in EP 1125637 A, corresponding to U.S. patent application Ser. No. 09/780287, which is incorporated herein by reference. On the other, e.g. by moving averaging, the dischargeable medium quantity can be determined in such a way that it does not exceed a specific, maximum concentration. It is also possible to allow the subsequent administration of small amounts of medium, which are intended to ensure that there is no exceeding of the maximum concentration, e.g. as a function of an assumed decomposition rate in the body. Thus, in a patient and also over long periods, it is possible to ensure that there are only slight concentration fluctuations as a result of frequent medicament administration, whilst simultaneously preventing an overdose.

Besides moving averaging, other methods are naturally usable for determining the maximum discharge quantity which can be discharged during the next discharge stroke.

Thus, it is e.g. possible to block a further discharge over a specific time period and then to continuously increase the maximum dischargeable dose over a specific, further time period until one or more complete operating strokes can be effected.

Figure 2:
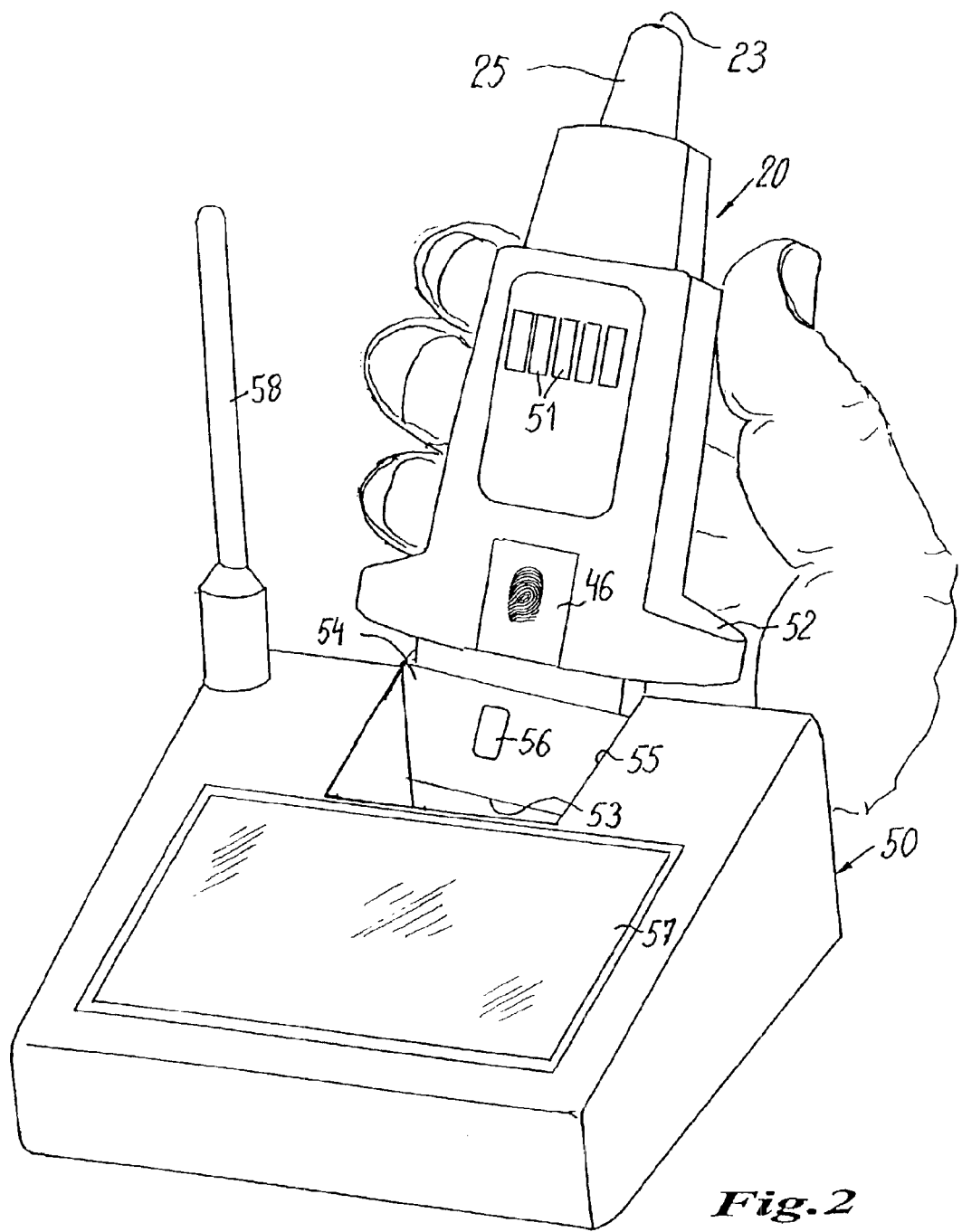
FIG. 2 shows a perspective view of a dispenser and a corresponding base station.

FIG. 2 shows the dispenser 20 which can be taken out of a base station 50 by hand. The base station 50 serves as storage for the dispenser 20. The dispenser is provided with displays 51 in form of LCD-fields, in which data can be shown. The dispenser 20 has laterally projecting shoulders 52 which can be held between two fingers of a user, while he manually operates the dispenser by exerting pressure to the operating surface 53. The operating surface 53 may include the sensor 46 of the identification device working by means of identifying a fingerprint of the authorized user (see FIG. 1). The sensor 46 may also be, as shown in FIG. 2, provided in a separate area at a sidewall of the dispenser.

In the actuation part 54 of the dispenser, which can be inserted into a corresponding recess 55 of the base station for storing, there is provided a connection or contact surface 56 for transferring data from the dispenser to the base station. This can be provided by an optocoupler, a galvanic contact, by inductive infrared transfer or by transponder.

The base station 50 contains a display 57 e.g. an LCD screen, on which data can be displayed. An antenna 58 for remote data transfer projects from the base station.

Figure 3:
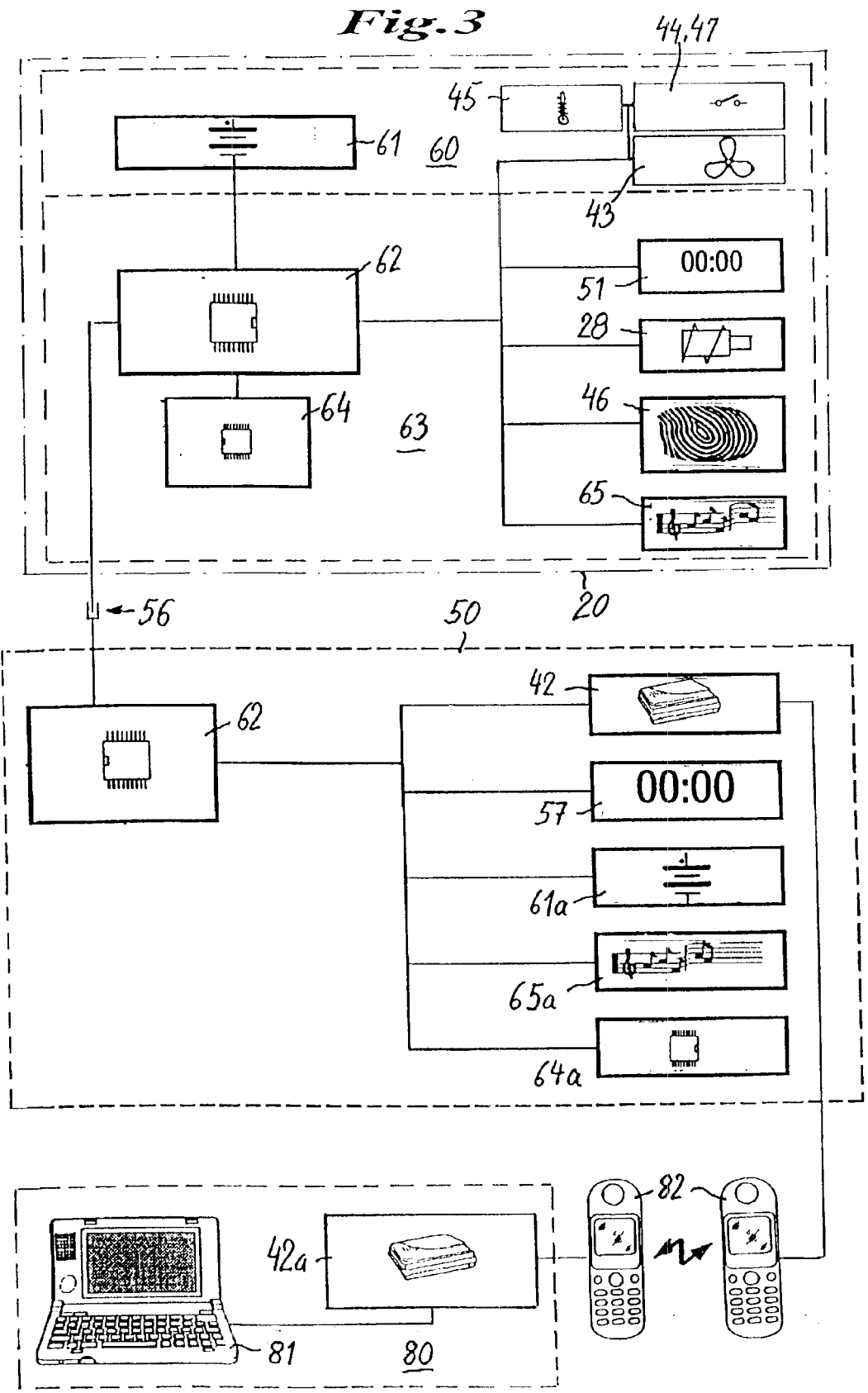
FIG. 3. shows a block diagram for explaining the cooperation of the dispenser with the sensors, the base station and an evaluation station.

FIG. 3 shows the data acquisition system according to the invention in diagrammatic block representation. The dispenser 20 contains an electric energy supply 61 consisting of a battery or an accumulator, which can be recharged via the base station 50. This part can be provided in a "throw away part" 60 of the dispenser which has to be separated from the rest of the dispenser and exchanged after each charge of medium or at least for every user. It contains also those of the sensors which may come into contact with the medium and/or the user and which have therefore, to be exchanged. This may be the temperature sensor 45, the path sensor 47 and the limit sensor 44 as well as the flow sensor 43. They feed their measured signals to a microcontroller or microcomputer 62 being situated in a re-usable 63 of the dispenser. The microcontroller, which is an electronic chip, is connected to an electronic memory 64. The microcontroller controls the polling of the data from the sensors and controls the acquisition and evaluating functions as well as mechanical functions of the dispenser including display, identification, servo functions and data transfer. FIG. 3 shows a display 51 (see also FIG. 2), the identification sensor 46, and an acoustic signal generator, e.g. a beeper or buzzer 65, and a servo device 28. The servo device 28 can be used for blocking the discharge stroke or varying the discharge stroke length, as already described with reference to FIG. 1.

The contact 56 is shown to symbolize the data output and transfer from the dispenser to the base station 50. The base station also contains a microcontroller or a microcomputer 62 together with the corresponding electric supply etc. (not shown). The microcontroller controls the following the devices and features of the base station 50: remote data transmission device 42, e.g. GSM modem, providing a data transmission connection to the mobile telephone network, the display 57, an electricity supply 61*a* (battery or mains operated), an acoustic single generator 65*a* and a memory 64*a*.

The base station evaluates and processes data from one or more dispensers in greater extent and is able to transfer to the microcomputers of the dispensers orders which can be general program orders or orders which are produced by the microcomputer as a result of incoming data, e.g. for the servo device 28.

The base station is also provided to transfer data, which are created in the dispenser and are processed there or in the base station via a remote data transfer device 42 to an external evaluation station 80. From this evaluation station 80 data can also be transferred into the base station and/or the dispenser. This can be done, as shown in FIG. 3 by using two mobile telephones 82 with data transfer ability and using a further GSM modem 42*a* in the evaluation station 80 which can be connected to a personal computer 81. The PC can process and evaluate the data automatically or be operated by a doctor or by corresponding operating persons, and send corresponding data back to the dispenser via the base station in order to automatically control and program it so as to achieve an ideal treatment for the patient.

What is claimed is:

1. Dispenser for a medium, said dispenser comprising:
   a storage container;
   a discharge opening;
   a medium path linking the storage container and the discharge opening;
   a delivery device for delivering medium from the storage container via the medium path to the discharge opening as a function of the operation of an operating device, said operating device comprising an electronic detecting unit for producing a signal representing the discharged medium quantity, the delivery device being a manually operable piston pump having a stroke path; and
   at least one sensor for detecting at least indirectly values representing the stroke path of the piston.

2. Dispenser according to claim 1, wherein the detecting unit comprises a flow volume meter located in the medium path.

3. Dispenser according to claim 2, wherein the flow volume meter is an inductive flow volume meter.

4. Dispenser according to claim 2, wherein the flow volume meter is a thermal flow volume meter.

5. Dispenser according to claim 2, wherein the flow volume meter determines the through-flow quantity on the basis of the pressure difference measuring method.

6. Dispenser according to claim 2, wherein the flow volume meter has a measuring range of 30 to 150 $\mu$l media volume.

7. Dispenser according to claim 1, wherein a limit switch is provided to detect an upper dead centre position of the pump piston after a complete pump stroke.

8. Dispenser according to claim 7, further comprising a device for additionally detecting the leaving of a lower dead centre position of the pump piston.

9. Dispenser according to claim 7, wherein the stroke path covered by the pump is detected by a path sensor.

10. Dispenser according to claim 1, wherein a time value is associated with each operation of the dispenser in the electronic detecting unit.

11. Dispenser according to claim 1, wherein in the detecting unit storing in pollable manner information detected with respect to a number of operations of the dispenser.

12. Dispenser according to claim 1, wherein a measuring sensor is located in the vicinity of the discharge opening, the sensor being at least one sensor selected from the group of sensors consisting of a thermal sensor, an optical sensor and a moisture sensor.

13. Dispenser according to claim 12, wherein the dispenser has a projection for fitting into a nostril, said projection including a tip, the discharge opening and measuring sensor being located in said tip of the projection.

14. Dispenser for a medium, said dispenser comprising:
a storage container;
a discharge opening;
a medium path linking the storage container and the discharge opening;
a delivery device for delivering the medium from the storage container via the medium path to the discharge opening as a function of the operation of an operating device said operating device comprising an electronic detecting unit for producing a signal representing the discharged medium quantity, the dispenser containing a servo device cooperating with the delivery device for controlling the function of said delivery device, and wherein said detecting unit controls said servo device.

15. Dispenser for a medium, said dispenser comprising:
a storage container;
a discharge opening;
a medium path linking the storage container and the discharge opening;
a delivery device for delivering the medium from the storage container via the medium path to the discharge opening as a function of the operation of an operating device said operating device comprising an electronic detecting unit for producing a signal representing the discharged medium quantity; and
a switchable operating barrier for blocking the discharge of medium under control of the detecting unit.

16. Dispenser according to claim 15, wherein the operating barrier is controlled as a function of at least a discharge volume of preceding discharge strokes and the time which has elapsed since then.

17. Dispenser for a medium, said dispenser comprising:
a storage container;
a discharge opening;
a medium path linking the storage container and the discharge opening;
a delivery device for delivering the medium from the storage container via the medium path to the discharge opening as a function of the operation of an operating device, said operating device comprising an electronic detecting unit for producing a signal representing the discharged medium quantity; and
a data exchange device through which the data detected by the detecting unit can be transmitted to at least one dispenser-external data processing device.

18. Dispenser according to claim 17, wherein the data exchange device is designed for bidirectional communication.

19. Dispenser according to claim 17, wherein said at least one external data processing device is a base station for storing the dispenser when not in use.

20. Dispenser according to claim 19, wherein said at least one external data processing device is an evaluation station, being in data transfer connection with the base station via a remote data transmitting system.

21. Dispenser for a medium, said dispenser comprising:
a storage container;
a discharge opening;
a medium path linking the storage container and the discharge opening;
a delivery device for delivering the medium from the storage container via the medium path to the discharge opening as a function of the operation of an operating device said operating device comprising an electronic detecting unit for producing a signal representing the discharged medium quantity;
the medium being a fluid containing at least one pharmaceutical substance.

22. Dispenser according to claim 21, wherein the dispenser is provided with a person identification sensor permitting an authentication of the user by means of characteristic features of the user.

23. Dispenser system for a medium comprising:
a dispenser having a storage container, a discharge opening, a medium path connecting the container with the opening, a manually operable pump between container and opening, a flow volume meter in the medium path producing electric signals, a data processing unit for receiving and processing the signals in order to generate data, an electronic memory for storing the data including data for time and number of pump operations, a data output dispenser;
further comprising an external station, having a data input for receiving the data from the data output, data output and input being connected in a wireless manner.

* * * * *